(12) United States Patent
Matsushita et al.

(10) Patent No.: US 7,501,241 B2
(45) Date of Patent: Mar. 10, 2009

(54) METHOD OF TRANSCRIBING BIOMOLECULAR PATTERNS, METHOD OF MANUFACTURING CHIP BOARDS, AND METHOD OF MANUFACTURING BIOCHIPS

(75) Inventors: Tomohiko Matsushita, Kadoma (JP); Shigeru Aoyama, Kyoto (JP); Takeo Nishikawa, Ibaraki (JP); Yuko Tsuda, Tokyo (JP); Shigemi Norioka, Ibaraki (JP); Tetsuichi Wazawa, Suita (JP)

(73) Assignee: OMRON Corporation, Kyoto (JP)

( * ) Notice: Subject to any disclaimer, the term of this patent is extended or adjusted under 35 U.S.C. 154(b) by 85 days.

(21) Appl. No.: 10/902,495

(22) Filed: Jul. 29, 2004

(65) Prior Publication Data
US 2005/0046758 A1 Mar. 3, 2005

(30) Foreign Application Priority Data
Jul. 29, 2003 (JP) ............................. 2003-202885

(51) Int. Cl.
*C12Q 1/68* (2006.01)
*C12M 1/34* (2006.01)
*C08L 89/00* (2006.01)
*A61K 8/73* (2006.01)

(52) U.S. Cl. ..................... 435/6; 435/287.1; 435/287.2; 524/17; 524/27

(58) Field of Classification Search ........................ None
See application file for complete search history.

(56) References Cited

U.S. PATENT DOCUMENTS

| | | | | |
|---|---|---|---|---|
| 4,108,740 A | * | 8/1978 | Wearmouth | 101/348 |
| 5,436,764 A | * | 7/1995 | Umetani et al. | 359/566 |
| 5,458,985 A | * | 10/1995 | Isono et al. | 428/601 |
| 5,994,110 A | | 11/1999 | Mosbach et al. | |
| 6,171,710 B1 | * | 1/2001 | Ogino et al. | 428/559 |
| 6,190,838 B1 | * | 2/2001 | Kerfeld | 430/320 |
| 6,485,984 B1 | | 11/2002 | Kim | |
| 6,489,418 B1 | * | 12/2002 | Mosbach | 526/238.1 |
| 2001/0049108 A1 | * | 12/2001 | McGall et al. | 435/6 |
| 2002/0045275 A1 | * | 4/2002 | Huang | 436/518 |

OTHER PUBLICATIONS

Jones et al, Anal. Chem., vol. 70, pp. 1233-1241 (1998).*
Mitra et al, J. Mater. Res, vol. 16, pp. 1010-1027 (2001).*

* cited by examiner

*Primary Examiner*—B J Forman
*Assistant Examiner*—Robert T. Crow
(74) *Attorney, Agent, or Firm*—Osha • Liang LLP

(57) ABSTRACT

A method of mass-producing minute structures such as biochips, protein chips, quantum dots, and quantum chips involves arranging an antigen two-dimensionally on a board and arranging probes two-dimensionally facing the same direction so that the binding sites of the probes may bind to the antigen. An inorganic substance such as Ni is deposited on the board from the upper side of the probes by sputtering or evaporation to form a thin film layer and on the top surface of the flatly formed thin film layer, a supporting layer is formed by separating out the same inorganic substance using electro-typing. Then, by peeling the thin film layer and the supporting layer off of the board together, the mother stamper having cavities for the patterns of biomolecules is obtained.

11 Claims, 16 Drawing Sheets

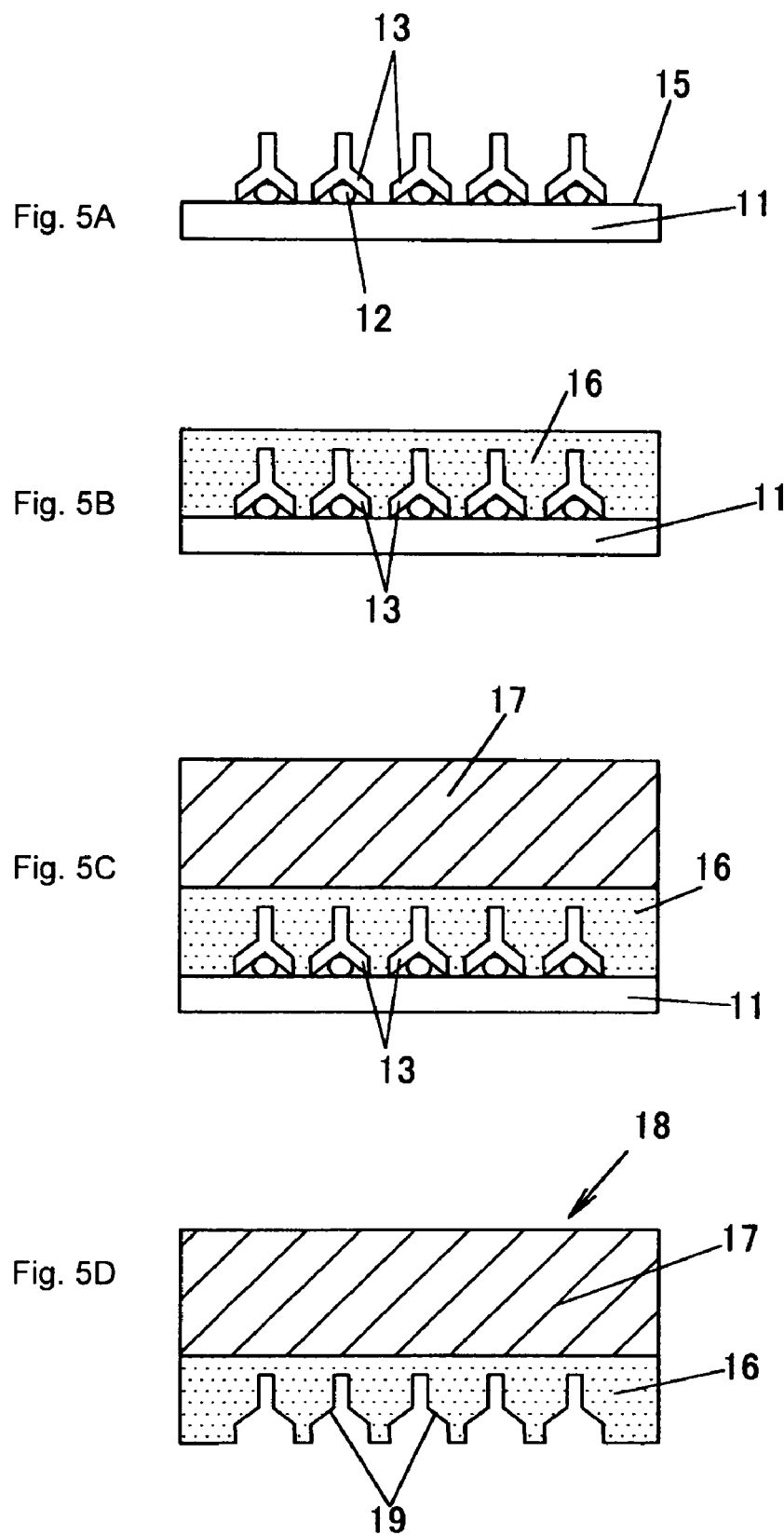

METHOD OF TRANSCRIBING BIOMOLECULAR PATTERNS, METHOD OF MANUFACTURING CHIP BOARDS, AND METHOD OF MANUFACTURING BIOCHIPS

BACKGROUND OF THE INVENTION

Biochips, on which biomolecules, such as DNAs or proteins, have been two-dimensionally arranged, are commonly used in studies on medical treatment and environmental conservation. In particular, protein chips, on which protein molecules (hereinafter, simply referred to as proteins) are two-dimensionally arranged on a chipboard, are being developed aiming at the applications including diagnosis, drug development, identity recognition, and biological system analysis.

A various kinds of probes (proteins) are arranged and immobilized on the chip board of a protein chip. Making samples such as blood contact with these proteins allows only specific targets (proteins) in the samples depending on the structures of the individual probes to binds to the probes. This means that the type of the target protein can be identified and the expression mechanism of proteins and the interaction among them can be also elucidated by converting any change in probe characteristic due to binding to the probe into an optical or electrical signal and reading it. Assuming that antibodies are used as probes, only specific antigens (antigens to specific viruses such as anthrax and smallpox) absorbed on the protein chip through the reaction with these antibodies and thereby, it can be determined whether the specific antigens harbor in the sample. Moreover, the quantity of antigens absorbed on the antibodies and the quantity of antigens removed from the sample are also capable of being determined.

However, as shown in FIG. 1, if a probe 1 has been arranged on a chip board 3 facing an arbitrary direction, the probe 1, which has not been correctly arranged, is not capable of absorbing a target 4.

Furthermore, a non-specific protein 5 may be caught within a gap formed around the probe 1 facing the arbitrary direction or the probe 1, which has been once immobilized on a chip board 3, may come away from the chip board 3 due to time-course changes and external factors.

SUMMARY OF THE INVENTION

A method of transcribing of the present invention is characterized in it involves a first step for two-dimensionally arranging biomolecules on a board, a second step for forming a thin film layer made of an inorganic substance on the biomolecules, a third step for forming a supporting layer on the thin film layer, and a fourth step for peeling the thin film layer and the supporting layer off from the biomolecules.

The implementation of the first to fourth steps according to the method of transcribing the biomolecules of the present invention allows the patterns of nano-scale biomolecules can be transcribed on a template composed of the thin film layer and the supporting layer. In addition, the substitution of nano-scale patterns for the biomolecules enables nano-scale patterns to be also transcribed.

According to an aspect of the method of transcribing the patterns of biomolecules of the present invention, at least one of hydrophilic, hydrophobic, and electrifying treatments is applied to an segment on the board other than that where the biomolecules are arranged before biomolecules are arranged in the first step. The biomolecules such as proteins have such characteristics as hydrophilicity, hydrophobicity, and electrostatic property and thereby, the hydrophilic, hydrophobic, or electrifying pre-treatments in the given segment of the board enables the biomolecules to be arranged in the given segment, facilitating well-ordered arrangement.

According to another aspect of the method of transcribing biomolecules of the present invention of the present invention, the biomolecules are two-dimensionally arranged on the board by two-dimensionally arranging the antigens on the board and binding the biomolecules the antigens in the first step. Antigens are capable of being relatively easily two-dimensionally arranged and thereby, biomolecules may be two-dimensionally arranged by two-dimensionally arranging antigens on a board and then binding the biomolecules to the arranged antigens so that they may face to the same direction.

Accordingly further another aspect of the method of transcribing the patterns of biomolecules of the present invention, the top of the thin film layer is flatly formed in the second step. The flat formation of the top of a thin film layer makes it difficult that a gap is formed between the thin film layer and the supporting layer and thereby, the strength of a template made of the thin film and supporting layers may be increased, stabling the accuracy of replication.

Accordingly more further another aspect of the method of transcribing biomolecules of the present invention, the thin film layer is formed by spattering or evaporating an inorganic substance in the second step and the supporting layer is formed by electrotyping the same inorganic substance as that of the thin film layer in the third step. The patterns of biomolecules can be transcribed by forming the thin film layer using spattering or evaporation. On the other hand, to form the thin film layer having a thickness with sufficient strength provided, a very long time period is required. To avoid this problem, the thin film layer is formed by sputtering or evaporation and the supporting layer is formed on it by electrotyping, thereby, the total film-formation time being reduced and the strength of the template being increased. The formation of the thin film and supporting layers using the same inorganic substance prevents them from peeling off one another.

Accordingly more further another aspect of the method of transcribing biomolecules of the present invention, in forming the supporting layer by electrotyping, an electrolytic solution of which pH value is almost the same as that of biomolecules is used in electrotyping. This prevents any alteration from occurring in biomolecules due to the electrolytic solution.

Accordingly more further another aspect of the method of transcribing biomolecules of the present invention, the particle size of the inorganic substance composing the thin film layer is less than 50 nm. Reduction in particle size of the inorganic substance composing the thin film layer, in particular, reduction in particle size to less than 50 nm, the patterns of nano-scale biomolecules can be accurately replicated.

Accordingly more further another aspect of the method of transcribing biomolecules of the present invention, the film thickness of the thin film layer is less than 200 nm. Note that the film thickness of the thin film layer should be higher than the height of the biomolecules. When the film thickness of the thin film layer is less than 200 nm, the film-forming process requires less time period.

According to the method of transcribing the patterns of biomolecules, the substitution of the biomolecules for nano-scale patterns enables the nano-scale patterns to be also transcribed.

The method of manufacturing a chip board of the present invention is characterized in that it involves a first step for two-dimensionally arranging biomolecules on a board, a second step for forming a thin film layer made of an inorganic substance on the biomolecules, a third step for forming a supporting layer on the thin film layer, a fourth step for obtaining a first stamper having concave parts of the reversed patterns of the biomolecules by peeling the thin film layer and the supporting layer off from the biomolecules, a fifth step for a fifth step for manufacturing a second stamper having the patterns replicated from the biomolecular patterns, templates, using the first stamper, and a sixth step for manufacturing the duplicating patterns of the first stamper using the second stamper.

According to the method of manufacturing the chip board of the present invention, the implementation of the first to sixth steps allows the chip board, on which the patterns of the biomolecules are accurately transcribed, to be mass-produced.

According to an aspect of the method of manufacturing the chip board of the present invention, the biomolecules are two-dimensionally arranged on the board using the self assembly feature of biomolecules in the first step. The arrangement of biomolecules on the board using the self assembly feature of the biomolecules enables nano-scale biomolecules to be two-dimensionally arranged easily in a convenient process, facilitating well-ordered arrangement.

The method of manufacturing a first biochip of the present invention is characterized in that it involves a first step for two-dimensionally sequencing biomolecules on a board, a second step for forming a thin film layer made of an inorganic substance on the biomolecules, a third step for forming a supporting layer on the thin film layer, and a fourth step for peeling the board off.

According to the method of manufacturing the first biochip of the present invention, the implementation of the first to fourth steps allows the biochip, which is arranged and immobilized so that the biomolecules face to the desired direction, to be obtained.

The method of manufacturing a second biochip of the present invention is characterized in that it involves a first step for two-dimensionally arranging biomolecules on a board, a second step for forming a thin film layer made of an inorganic substance on the biomolecules, a third step for a forming a supporting layer on the thin film layer, a fourth step for obtaining a first stamper having the concave parts of the reversed patterns of the biomolecules by peeling the thin film layer and the supporting layer together off from the biomolecules, a fifth step for manufacturing a second stamper having the patterns replicated from the biomolecular patterns, templates, using the first stamper, a sixth step for manufacturing the replicating patterns of the first stamper using the second stamper, and a seventh step for immobilizing given biomolecules in concave parts disposed at the replicating patterns of the first stamper.

According to the method of manufacturing the second biochip of the present invention, the implementation of the first to seventh steps allows the biochip, which is arranged and immobilized so that the biomolecules face to the desired direction, to be mass produced.

The chip board of the present invention is characterized in that a first step for two-dimensionally arranging structures on a board, a second step for forming a thin film layer made of an inorganic substance on the structures, a third step for a forming a supporting layer on the thin film layer, a fourth step for obtaining a stamper having the reversed patterns of the structures by peeling the thin film layer and the supporting layer together off from the structures, and a fifth step for manufacturing the patterns replicated from the patterns, templates, using the stamper, ad thereby, the ship board, on which nano-scale structures are replicated, is capable of being mass produced.

Note that the components of the present invention mentioned above may be combined in any manner as much as possible.

BRIEF DESCRIPTION OF DRAWINGS

FIGS. 5A, 5B, 5C, and 5D explain the schematic manufacturing process of a mother stamper according to the first embodiment of the present invention.

DETAILED DESCRIPTION

Now, the embodiments of the present invention will be described in detail giving an example of the case where a protein chip or a momentum device is replicated.

First Embodiment

The process of manufacturing a first protein chip of the present invention is composed mainly of (1) a step for manufacturing a master protein chip, (2) a step for manufacturing a mother stamper by replication, (3) a step for manufacturing a stamper, (4) a step for manufacturing a chip board, and (5) a step for manufacturing a replicated protein chip.

(Manufacturing a Master Protein Chip)

Figure 1:
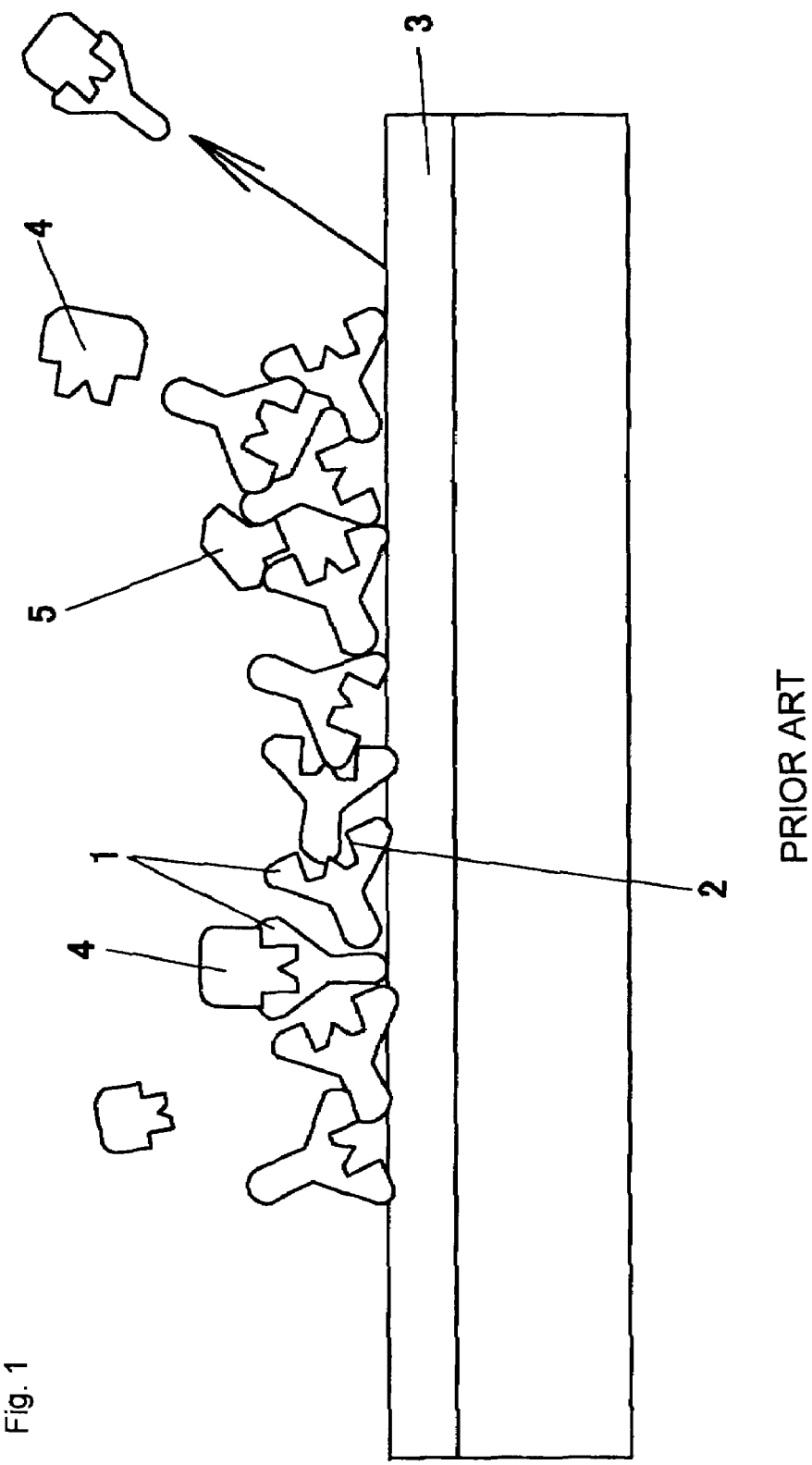
FIG. 1 shows the probes arranged on a conventional protein chip board.
Figure 2A:
FIGS. 2A, 2B, and 2C show the schematic manufacturing process of a master protein chip according to the first embodiment of the present invention.
Figure 2B:
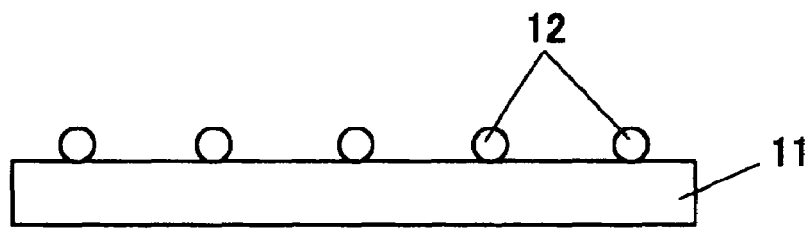
Figure 2C:
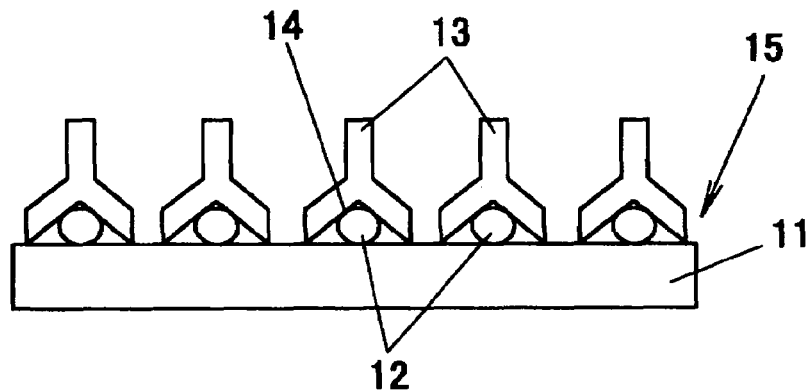

FIGS. 2A, 2B, and 2C show a schematic manufacturing process of a master protein chip 15. As shown in FIG. 2A, first of all, a board 11, for example, a clean silica glass board with no dirt attached after being washed and dried, is prepared. Then, an antigen 12 to be bound to a specific protein as a probe is selected and as shown in FIG. 2B, only one layer of the antigen 12 is attached on the surface of the board 11 for arrangement. Assuming that the surface of the board 11 is pre-treated and then the bard 11 is immersed into in a solution containing the dissolved antigen 12, only one layer of antigen 12 is arranged on the surface of the board 11. However, the antigen 12 may not always arranged on the surface of the board 11 depending on the application of the protein chip.

Subsequently, when the board 11 is immersed in the solution containing dissolved probes 13, a specific protein, the binding site of the specific probes 13 in the solution binds to the antigen 12 and as shown in FIG. 2C, the specific probes 13 is arranged with its binding site 14 facing downward on the surface of the board 11 and thereby, the master protein chip is obtained. Thus, by the antigen 12 is arranged and attached on the surface of the board 11 in advance, the specific probes 13 can be arranged and immobilized on the surface of the board 11 so that they may face to the same direction. The selection of the type of the antigen 12 allows the type of the probes 13, which is to specifically bind to it, to be also selected.

Although for a master protein chip 15, the probes 13 are attached on the whole surface of the board 11, it may be desired that the probes 13 are selectively immobilized only on the certain segment of the board 11. For example, it may be desired that the surface of the board 11 are split into a plurality of segments and different proteins (for example, probes which traps the unique protein excreted by anthrax or an antigen or probes which traps the unique protein excreted by smallpox virus or an antigen) are immobilized their corresponding segments to detect a plurality of antigens at the same time.

Figure 3A:
FIGS. 3A, 3B, and 3C show the schematic method of immobilizing the probes selectively on the certain segments of the board in the master protein chip manufacturing process.
Figure 3B:
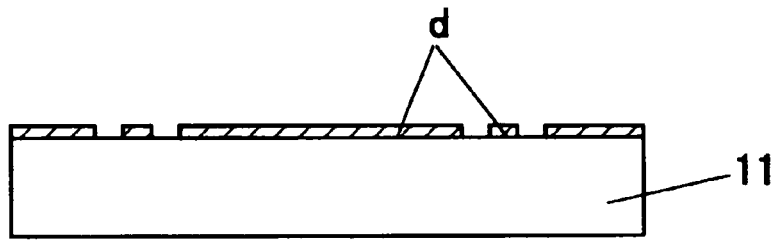
Figure 3C:
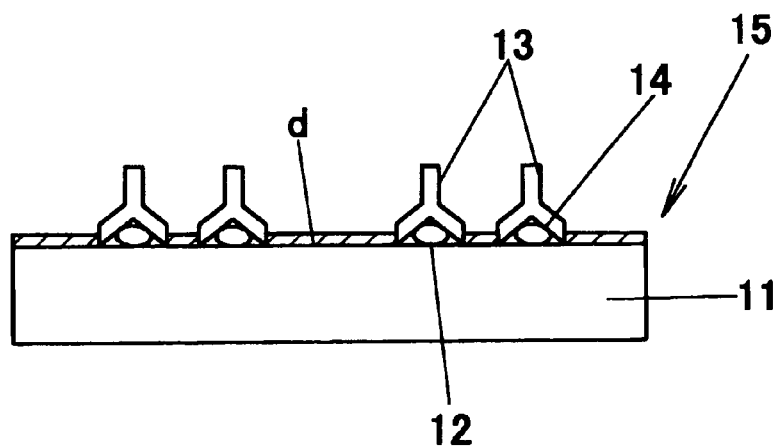

FIGS. 3A, 3B, and 3C show steps in the case where the probes 1 are to be selectively immobilized on the certain segment. First of all, as shown in FIG. 3A, a board 11, for example a clean silica glass with no dirt is prepared. Then, as shown in 3B, one of hydrophilic, hydrophobic, and electrifying pre-treatments is partially applied to a segment d other than that where the probes 1 are to be immobilized. Patterning may be applied to the pre-treated segment d in advance. The method of pre-treating the segment includes chemical application using an ink-jet type printer, film formation using photolithography, and electrifying using leaser or electronic beam irradiation. Depending on the property of the probes 13 to be immobilized, the application of any of the hydrophilic, hydrophobic, or electrifying pre-treatments to the probes 13 with inherent hydrophilic, hydrophobic, or electrified property prevents the probes 13 from attaching to the pre-treated segment. The type of pre-treatments is selected depending on the type of the protein to be immobilized. For example, in the case of the probes 13 having the hydrophilic property, the hydrophobic treatment is selected, while in the case of they are positively charged, the positively-electrifying treatment is selected.

In the untreated segments of the treated board 11, the antigen 12 is attached and arranged in the form of a single layer as mentioned above.

Subsequently, when the board 11 is immersed in the solution containing the dissolved probes 13, the binding groups 14 of the specific probes 13 in the solution are absorbed by the antigen 12 and immobilized on the board 11. Since no probes 13 are attached to the pre-treated segment d, the probes 13 are partially attached only to the untreated segment, forming patterns as shown in FIG. 3C.

Note that the board may be pre-treated so that the probes 13 may attach to the pre-treated segment.

Figure 4A:
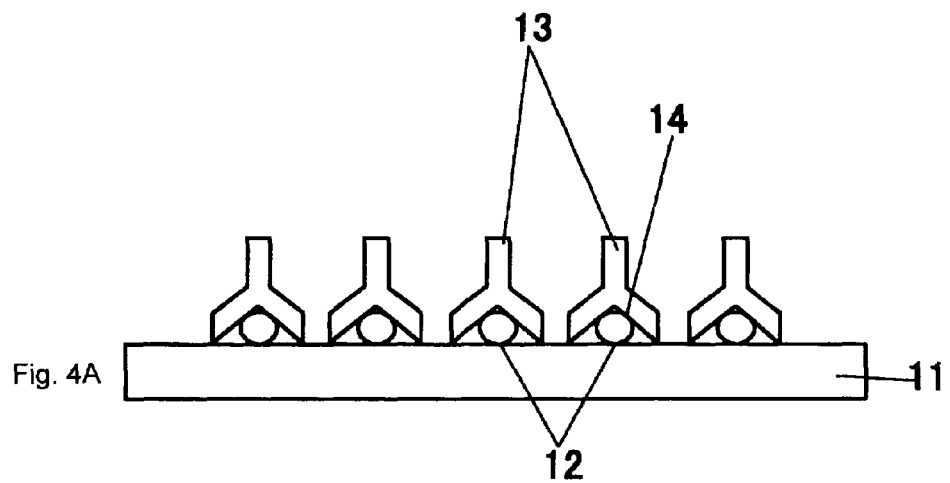
FIGS. 4A and 4B show another schematic method of immobilizing the probes selectively on the certain segments of the board in the master protein chip manufacturing process.
Figure 4B:
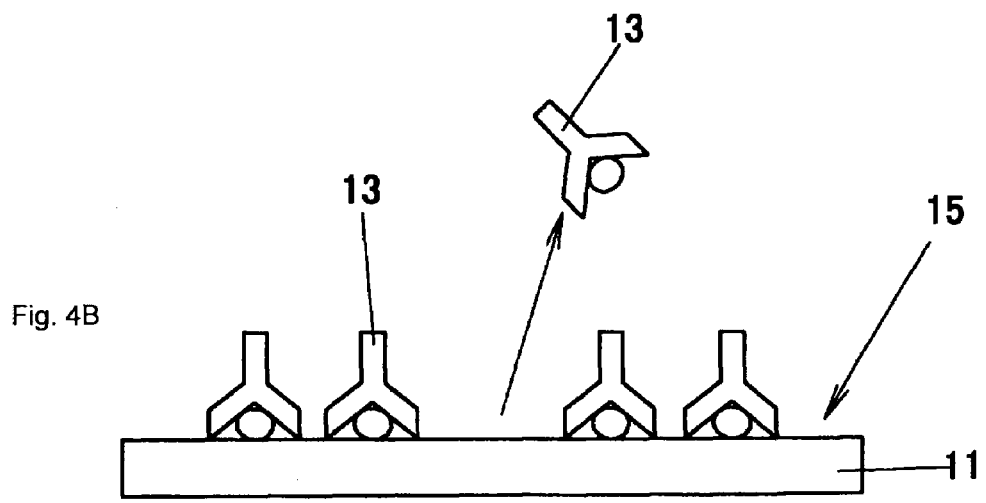

FIGS. 4A and 4B show another method of immobilizing the probes 1 selectively to the part of the board 1. As shown in 4A, (using the similar method to that shown in FIG. 2), with this method, the probes 13 were immobilized on the whole surface of the board 11 and then as shown in FIG. 4B, unwanted probes 13 were removed in the post-treatment step. For example, the method of physically removing the unwanted probes 13 includes the FIB (Focus Ion Beam) method which irradiates an ion beam on the board 11 and the method which uses Atomic Force Microscope. Alternatively, the unwanted probes 13 maybe only deactivated by irradiating electromagnetic waves such as laser without removing from the board 11.

(Manufacturing a Mother Stamper through Replication)

FIGS. 5A, 5B, 5C, and 5D show the manufacturing process of a mother stamper 18. A master stamper 15 is manufactured as mentioned above and then a mother stamper 18 is manufactured using the master stamper 15 as a template. FIG. 5A shows the master protein chip 15 manufactured as mentioned above. As shown in FIG. 5B, in this manufacturing process, an inorganic substance is deposited on the board 11 by sputtering or evaporation so that it may cover the probes 13 to form a thin film layer 16 with a flat surface and then as shown in FIG. 5C, a supporting layer 17 made of the inorganic substance is formed on the thin film layer 16 by electrotyping.

In this case, it is recommended to use the same material for the thin film layer 16 formed by sputtering or evaporation and for the supporting layer 17 formed by electrotyping. The use of the same material prevents the thin film layer 16 and the supporting layer 17 from peeling off one another at the interface formed between them. For the material for the thin film layer 16 and the supporting layer 17, metals such as Ni, Cu, Au, Ti, Ag, and Zn may be used and in particular, Ni is preferred. Ni minimizes internal stress possibly exerted in manufacturing the supporting layer 17 by electrotyping, best suited for the mother stamper because of its high hardness, and provides uniform film formation. It is recommended that for an electrolytic solution used to separate out the supporting layer 17 by electrotyping, the solution of the same pH as that of the protein, probes 13, is selected. This prevents the proves 13 immobilized on the master protein chip 15 to degenerate in forming the supporting layer 17, enabling precise replication of the pattern of the probes 13.

Alternatively, by reducing the size of particles deposited by sputtering or evaporation to less than 50 nm, the structures of the probe 13 with no gap can be transcribed, improving the transcription accuracy. To reduce the size of the particles composing the supporting layer 17 to less than 50 nm, the sputtering or evaporating conditions should be adjusted. In the sputtering or evaporating process, keeping the board at a lower temperature (lower than 40° C.) and slowing the deposition rate to reduce energy prevents the probes 13 from being deactivated.

It is desired that the thin film layer 16 is formed so that its thickness may be larger than the height (less than approximately several hundreds nm) of the probes 13 and it may have a flat surface. The flat formation of the surface of the thin film layer 16 prevents gaps from being formed between the thin film layer 16 and the supporting layer 17 in forming the supporting layer 17 on the thin film layer 16. In addition, the mother stamper 18 composed of two layers, the thin film and supporting layers, is improved.

On the other hand, if the thickness of the thin film layer 16 is more than 200 nm, the film formation process of the thin film layer 16 requires the elongated time. To avoid this problem, the thickness of the thin film layer 16 is reduced to less than 200 nm and the supporting layer 17 is formed by electrotyping with a higher film formation rate than those of sputtering and evaporation, shortening the process time as a whole for increasing manufacturing efficiency while improving the strength of the mother stamper 18.

By forming the mother stamper 18 composed of the thin film layer 16 and the supporting layer 17 on the master protein chip 15 in the manner mentioned above and peeling the thin film layer 16 and the supporting layer 17 together off from the master protein chip 15 as shown in FIG. 5D, the mother stamper 18 can be obtained. The mother stamper 18 has a plurality of cavities 19 where the patterns of the probes 13 have been transcribed. The probes 13 remaining in the cavities 19 are fully removed by, for example, irradiating oxygen plasma on them for burning out.

Note that the mother stamper 18 maybe constructed so that it has three or more layers, however, it is preferred for it to have a two-layer structure because more complicated process makes the time required for manufacturing the mother stamper 18 longer.

(Manufacturing a Stamper)

Figure 6A:
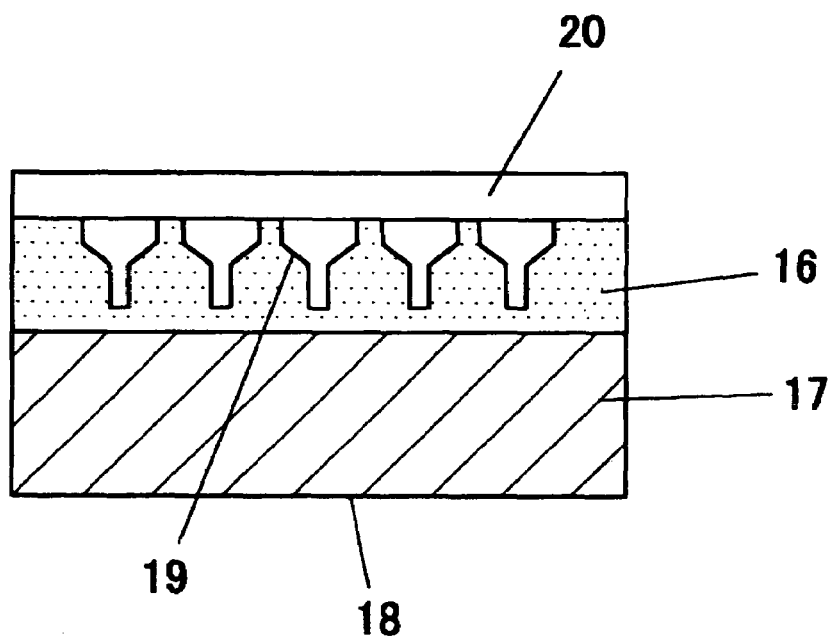
FIGS. 6A and 6B show the schematic manufacturing process of stampers according to the first embodiment of the present invention.
Figure 6B:
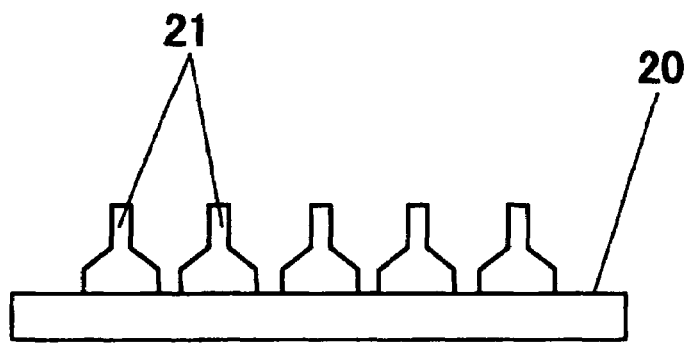

FIGS. 6A and 6B show schematic manufacturing process of a stamper 20. After the mother stamper 18 has been manufactured, a stamper 20, a reversed version of the mother stamper 18, is manufactured based on the mother stamper 18. In the manufacturing process of the stamper 20, as shown in FIG. 6A, the stamper 20 is manufactured by electrotyping or any other technique using the mother stamper 18 as a concave pattern. As shown in FIG. 6B, when the stamper 20 is peeled off from the mother stamper 18, a plurality of replicates 21 of probes 13 are formed on the stamper 20 by the cavities 19 of the mother stamper 18.

Thus, by manufacturing the stamper 20, a reversed version of the mother stamper 18, using the mother stamper 18, the same pattern as that of the protein chip 15, meaning that it may be applied in the manufacturing replicated protein chips. By manufacturing a plurality of stampers 20 using the mother stamper 18, a plurality of stampers 20 can be manufactured using a single master protein chip 15 and stored. This means that the manufacturing method is suited for the mass-production of replicated protein chips and capable of stabling the quality of the products.

(Manufacturing a Chip Board)

Figure 7A:
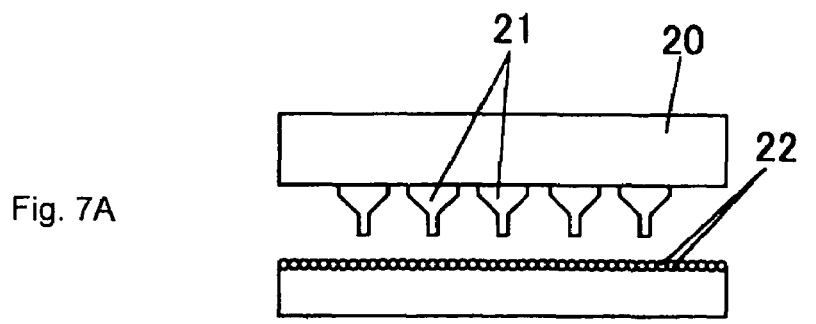
FIGS. 7A, 7B, 7C, and 7D show the schematic manufacturing process of a chip board according to the first embodiment of the present invention.

FIGS. 7A, 7B, 7C, and 7D show the schematic manufacturing process of a chip board 26. After the stamper 20 has been manufactured, a chip board 26 for replicated protein chips is manufactured using the stamper 20. In the manufacturing process of the chip board 26, first of all, as shown in FIG. 7A, the tip of a replicate 21 may be made contact with the layer of immobilizing molecules 22 (also referred to as modified molecules) with the replicates 21 of the stamper 20 facing downward attach the immobilizing molecules 22 locally to the tips of the individual replicates 21. The immobilizing molecules 22 are those which bind specifically to the sites opposite to the binding sites of the probes 13, including NTA derivatives, biotin, and avidin.

Figure 7B:
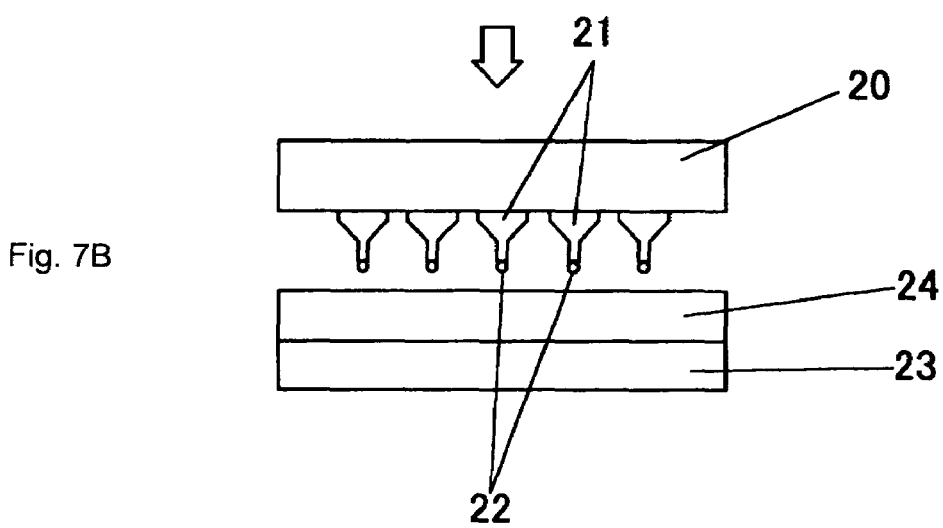
Figure 7C:
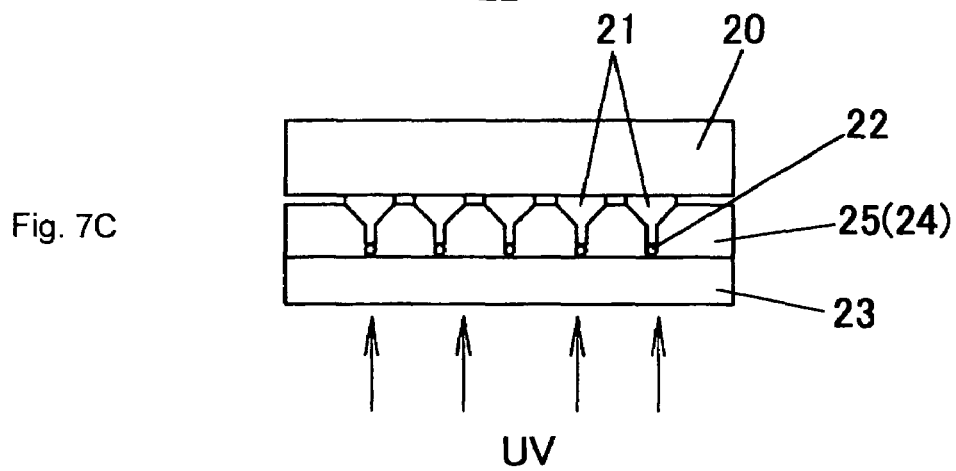
Figure 7D:
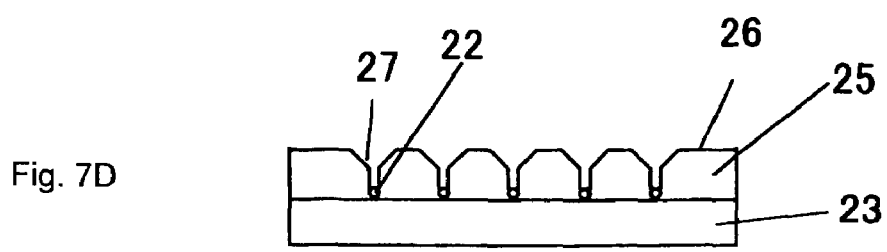

Then, as shown in FIG. 7B, the replicate 21 conserving the immobilizing molecules at its tip is pressed against a glass board 23 coated with uncured UV cure resin 24 to transcribe the pattern of the replicate 21 on the ultra violet (UV) cure resin 24. Subsequently, as shown in FIG. 7C, UV is irradiated on the UV cure resin 24 through the glass board 23 to cure the UV cure resin 24 and thereby, a surface layer 25 composed of the UV cure resin 24 is formed on the glass board 23. After then, by peeling off the stamper 20, the chip board 26, where a surface layer 25 is formed on the glass board 23, is obtained as shown in FIG. 7D. On the surface layer 25 of the chip board 26, a plurality of traps 27 having the reversed patterns of the replicates 21, namely the reversed patterns of the probes 13 have been formed in the form of concave and at the bottoms of the individual traps 27, the immobilizing molecules 22 remain. Note that the immobilizing molecules are not always used.

(Manufacturing Replicated Protein Chips)

Figure 8A:
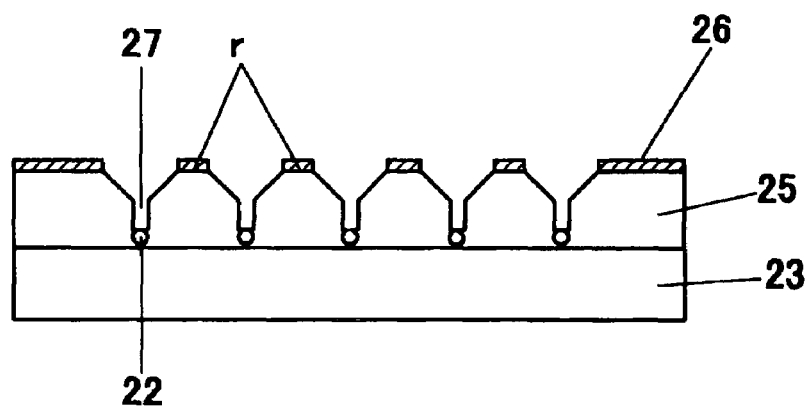
FIGS. 8A and 8B show the schematic manufacturing process of replicated protein chips according to the first embodiment of the present invention.
Figure 8B:
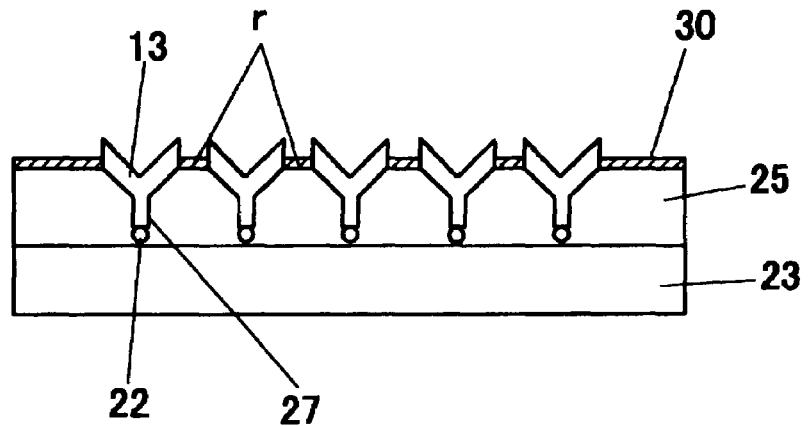

FIGS. 8A and 8B show the schematic manufacturing process of replicated protein chips 30. After the chip board 26 has been manufactured in the manner mentioned above, any of hydrophilic, hydrophobic, and electrifying pre-treatments is applied to a segment r other than a trap 27 on the surface of the chip board 26 as shown in FIG. 8A. The method of applying pre-treatment includes drug application using an ink-jet printer, film formation by photolithography, and electrifying treatment by irradiating laser or electron beam. The application of any pre-treatment to the probes 13 having a hydrophilic, hydrophobic, or electrified property depending on the property of the probes 13 to be immobilized prevents the proves 13 from being immobilized in any other segments than the trap 27. Note that the process shown in FIG. 8A may be omitted.

Figure 9:
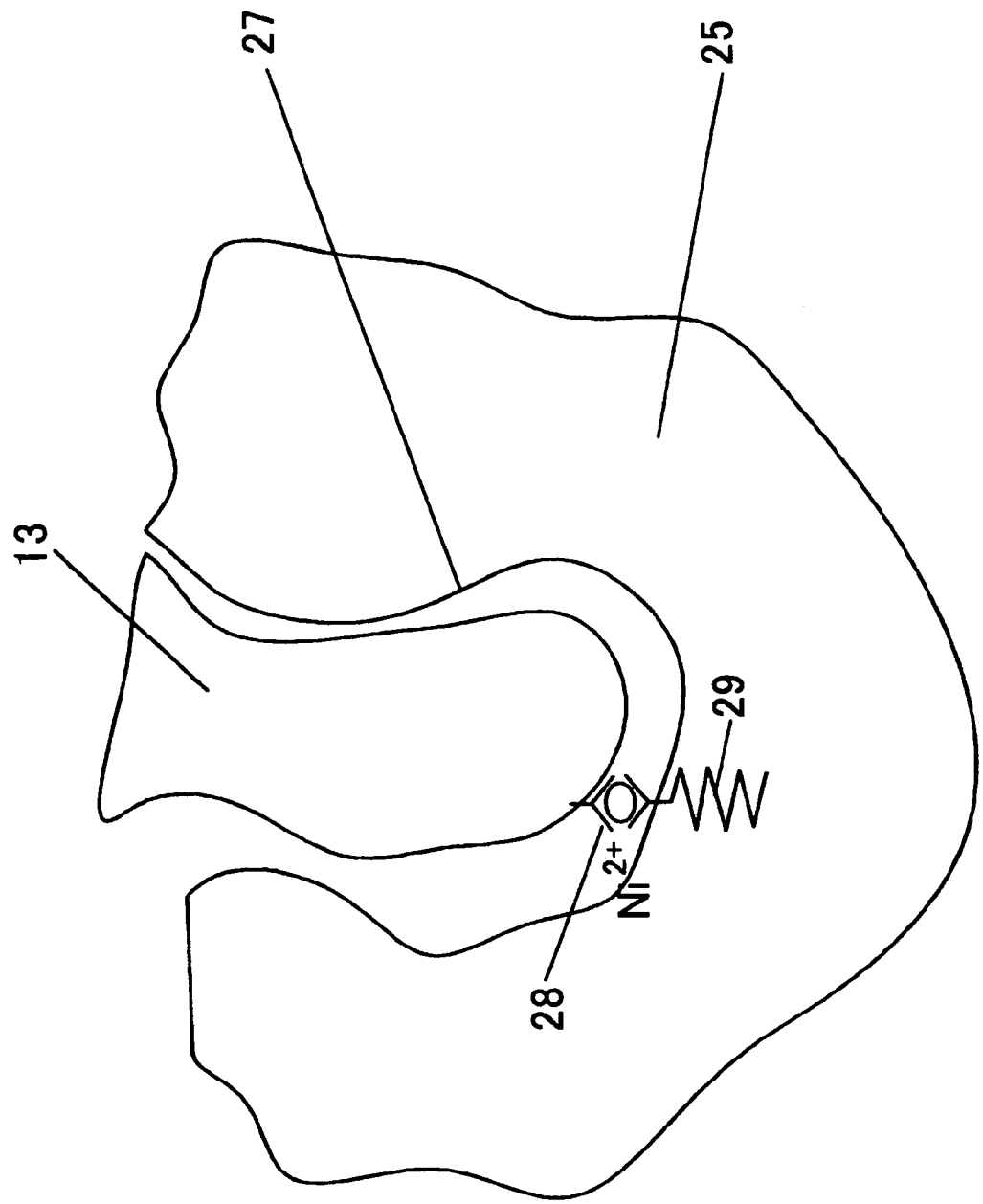
FIG. 9 shows the arrangement of the probes where the ends of the probes opposite to their binding sites have been immobilized on the chip board by immobilizing molecules.

Next, when the chip board 26 is immersed in the solution containing the dissolved probes 13, only the specific probes 13 (specific protein) having the same pattern as that of the trap 27 are selectively trapped within the trap 27 and immobilized on the chip board 26 by the immobilizing molecules 22 as shown in FIG. 8B. For example, if a His-Tag is labeled at the end opposite to the binding sites of the probes 13 and NTA derivatives are attached at the bottom of the trap 27 as the immobilizing molecules 22, His-Tag 28 and $Ni^{2+}$ of the NTA derivatives 29 are bound one another to immobilize the probes 13 within the trap 27 as shown in FIG. 9. His-Tag 28 described here can be labeled to the probes 13 using a genetic engineering technique at any position freely and conveniently as much as possible, preventing the probes 13 from being deactivated. The pre-treatment applied to other segments than the trap prevents the probes 13 from being immobilized in any other segments than the trap 27. Thus, replicated protein chips 30 are manufactured as shown in FIG. 8B.

Figure 10:
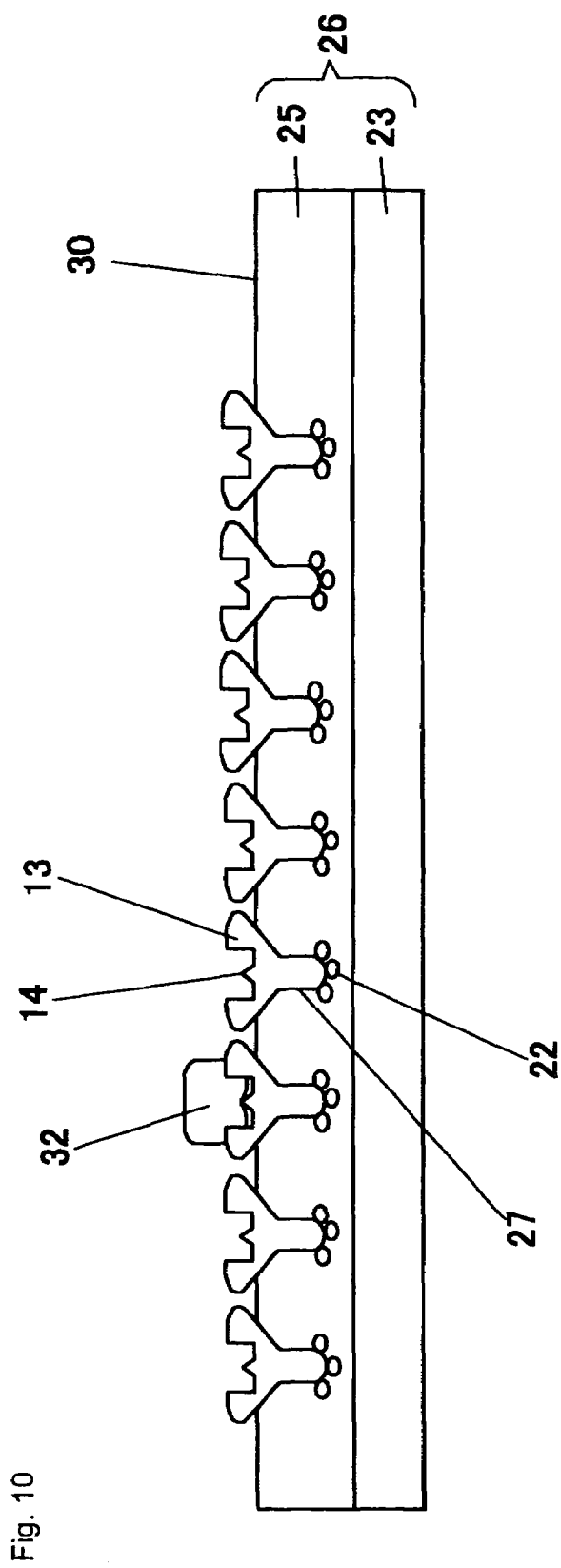
FIG. 10 shows the enlarged cross section of the replicated protein chip of the present invention.

FIG. 10 shows the enlarged cross section of the replicated protein chip 30 manufactured as mentioned above. On the replicated protein chip 30, the chip board 26 has been formed by forming the resin-made surface layer 25 on the glass board 23, and on the surface layer 25, a plurality of arranged traps 27 are formed in the form of concave. At the bottoms of the individual traps 27, the immobilizing molecules are trapped, and the specific probes 13 are immobilized by the immobilizing molecules 22 in the individual traps 27 having the same patterns as those of the probes 13. The individual proves 13 trapped on the surface of the replicated protein chip 30 are capable of absorbing the given targets 32 efficiently at their binding sites 14 because the binding sites 14 face upward. Note that the pre-treatment applied in the segment r may be left or removed.

Second Embodiment

The second manufacturing process of protein chips of the present invention involves mainly (1) a step for manufacturing a master protein chip and (2) a step for forming a protein chip board composed of a thin film and supporting layers.

First of all, the master protein chip 15 is manufactured according to the similar process to that of the first embodiment. Then, the thin film layer 16 and the supporting layer 17 are manufactured according to the similar process to that of the first embodiment. Subsequently, when only the board 11 is peeling off so that the thin film layer 16 and the supporting layer 17 may remain there, the protein chip where the probes 13 are immobilized on the protein chip composed of the thin film layer 16 and the supporting layer 17 is obtained. In the case where The antigen 12 is attached to the probes 13, the antigen 12 should be removed.

According to the second embodiment of the present invention, the protein chip with the proteins immobilized facing to the desired same direction, though the mass-productivity is not superior to the first embodiment of the present invention.

Third Embodiment

According to the first embodiment of the present invention, the mother stamper 18 manufactured during the process of manufacturing replicated protein chips can be used as quantum devices such as quantum dots and photonic crystals. When they are used as quantum devices, the probes may be two-dimensionally arranged on the chip board using the self assembly feature of the biomolecules instead of the antigen 12 to manufacture the mother stamper 18. The proteins, which may be two-dimensionally arranged, include ferritin, catalase, chavellonine, SRCa$^{2+}$ATP splitting enzyme, tubulin, streptoavidin, and rhodopsin. Proteins are not always used.

Figure 11A:
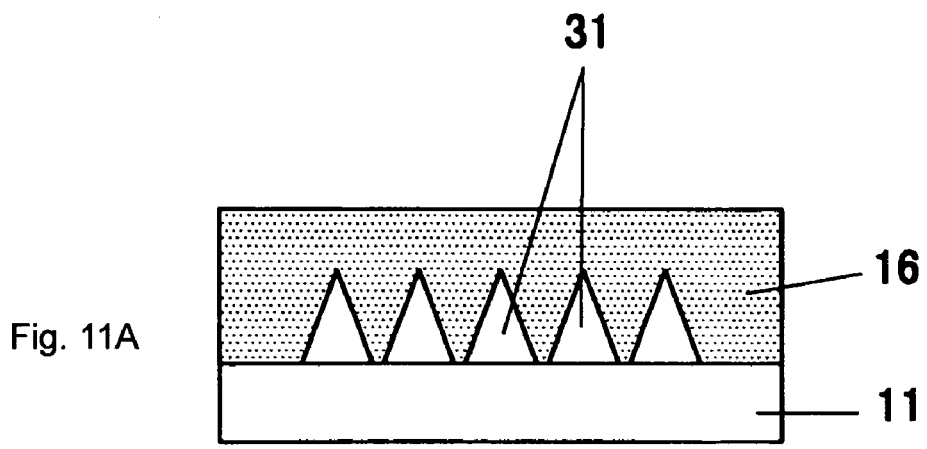
FIGS. 11A, 11B, and 11C show the schematic manufacturing process of the replicates of nano-scale structures such as atoms, molecules, and crystals on the board according to the first embodiment of the present invention.
Figure 11B:
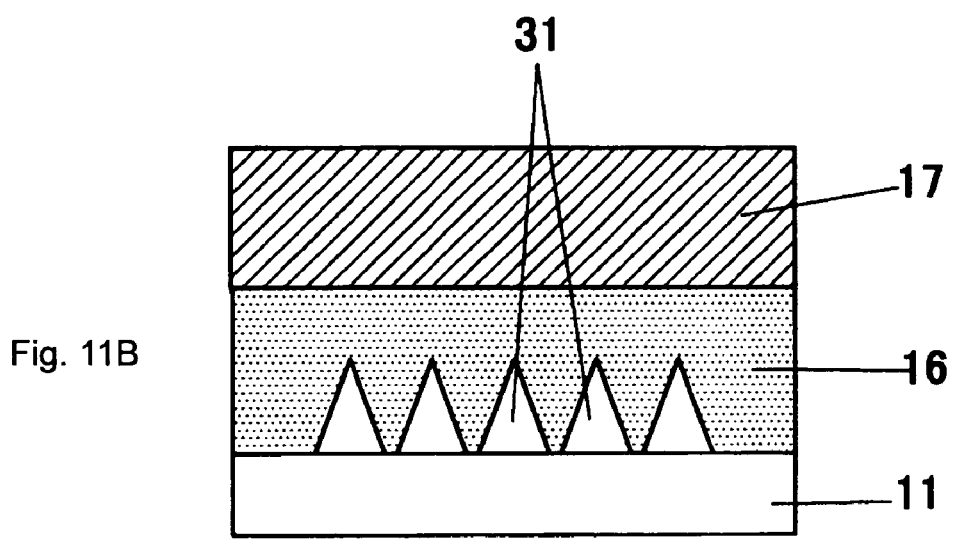
Figure 11C:
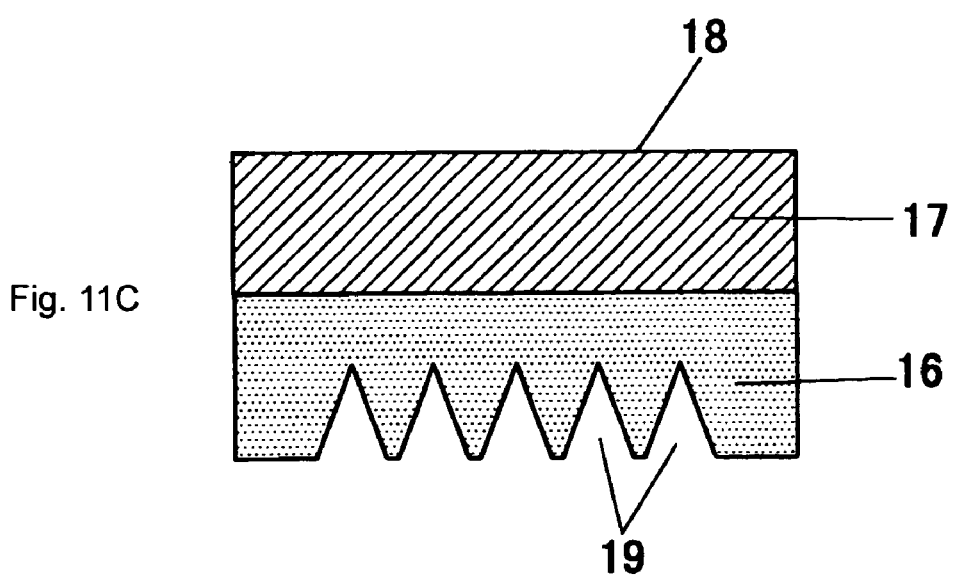

For example, as shown in FIG. 11A, after the nano-scale structures 31 such as atoms, molecules, and crystals have been arranged on the surface of the board 11, the thin film layer 16 is formed by depositing an inorganic substance on the structures 31 by sputtering or vacuum evaporation. Then, as shown in FIG. 11B, the supporting layer 17 is made of the same inorganic substance on the thin film layer 16 by electrotyping. In this case, assuming that the size of the particles composing the thin film layer 16 is less than 50 nm, the pattern of the nano-scale structures 31 can be precisely transcribed. Subsequently, by peeling the structures 31 and the board 11 off, the mother stamper 18 composed of the thin film layer 16 and the supporting layer 17 is obtained and on the bottom surface of the mother stamper 18, cavities 19, a reversed version of structures 31 are formed as shown in FIG. 11C.

Figure 12A:
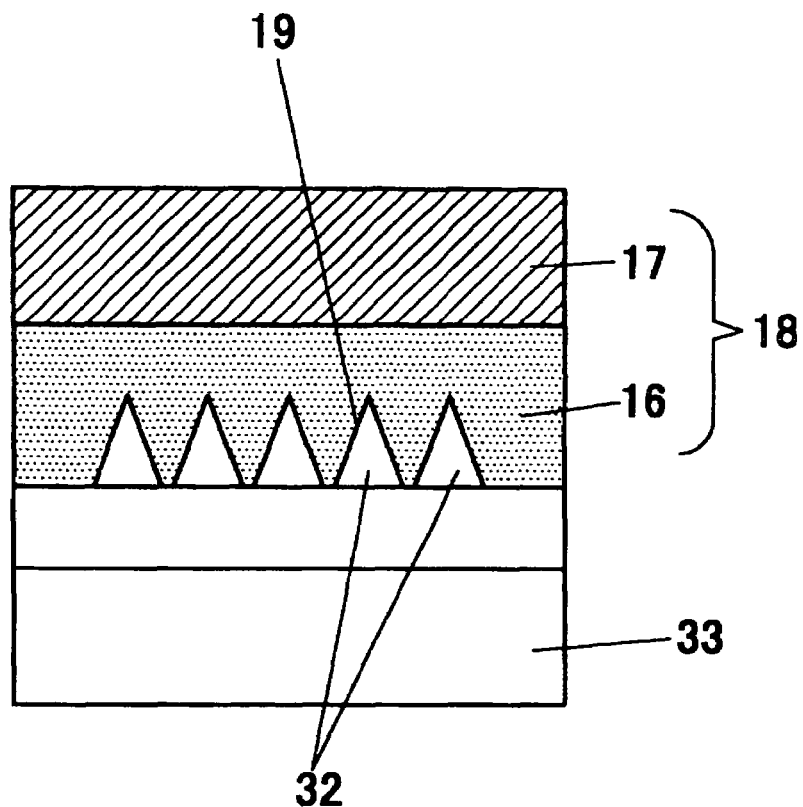
FIGS. 12A and 12B show the schematic manufacturing process of the replicates of nano-scale structures on the board using the mother stamper mentioned above.
Figure 12B:
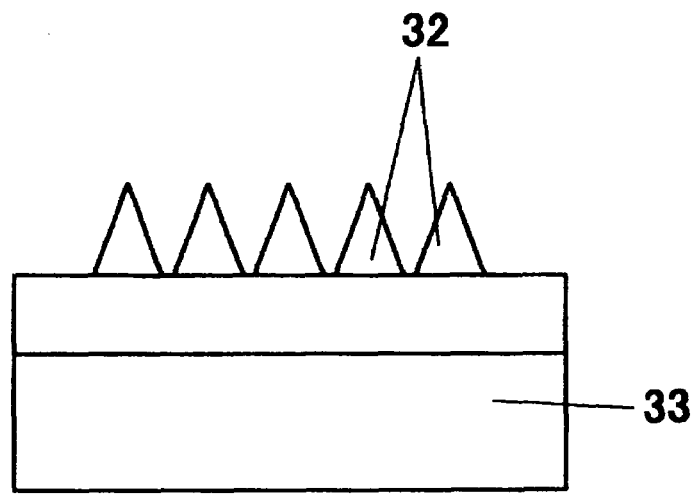
Figure 13:
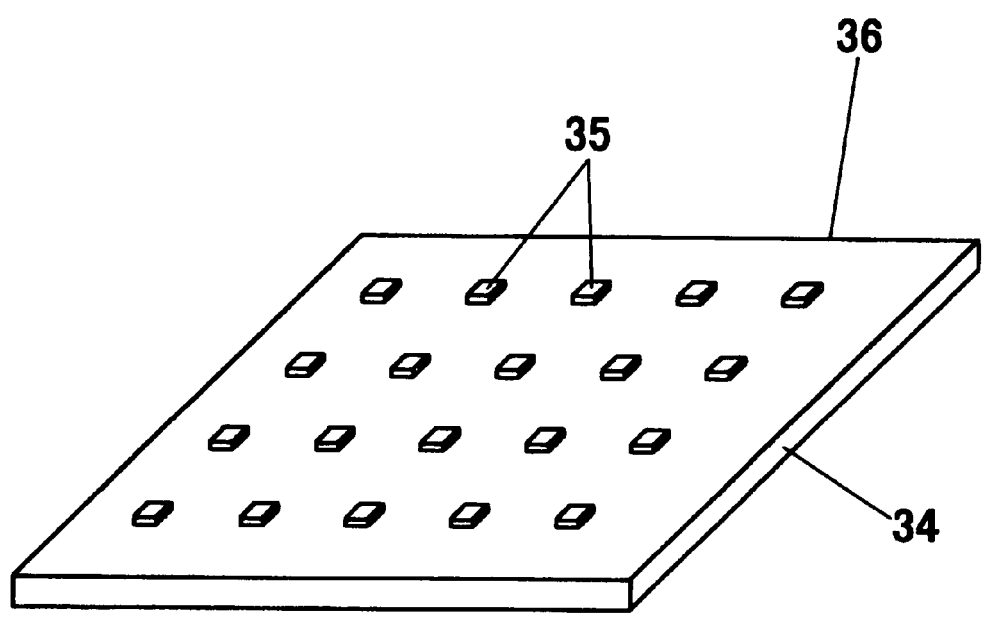
FIG. 13 shows quantum dots formed on the board from the perspective point of view.

Subsequently, as shown in FIG. 12A, by forming any resin or metal material using the mother stamper 18, the replicates 32 replicated from the nano-scale structures 31 are formed on the board 33 as shown in FIG. 12B. The replicates 32 manufactured in this way can be used for the quantum dots, quantum fine lines, and quantum wells. They may be also used for photonic crystals.

Figure 14:
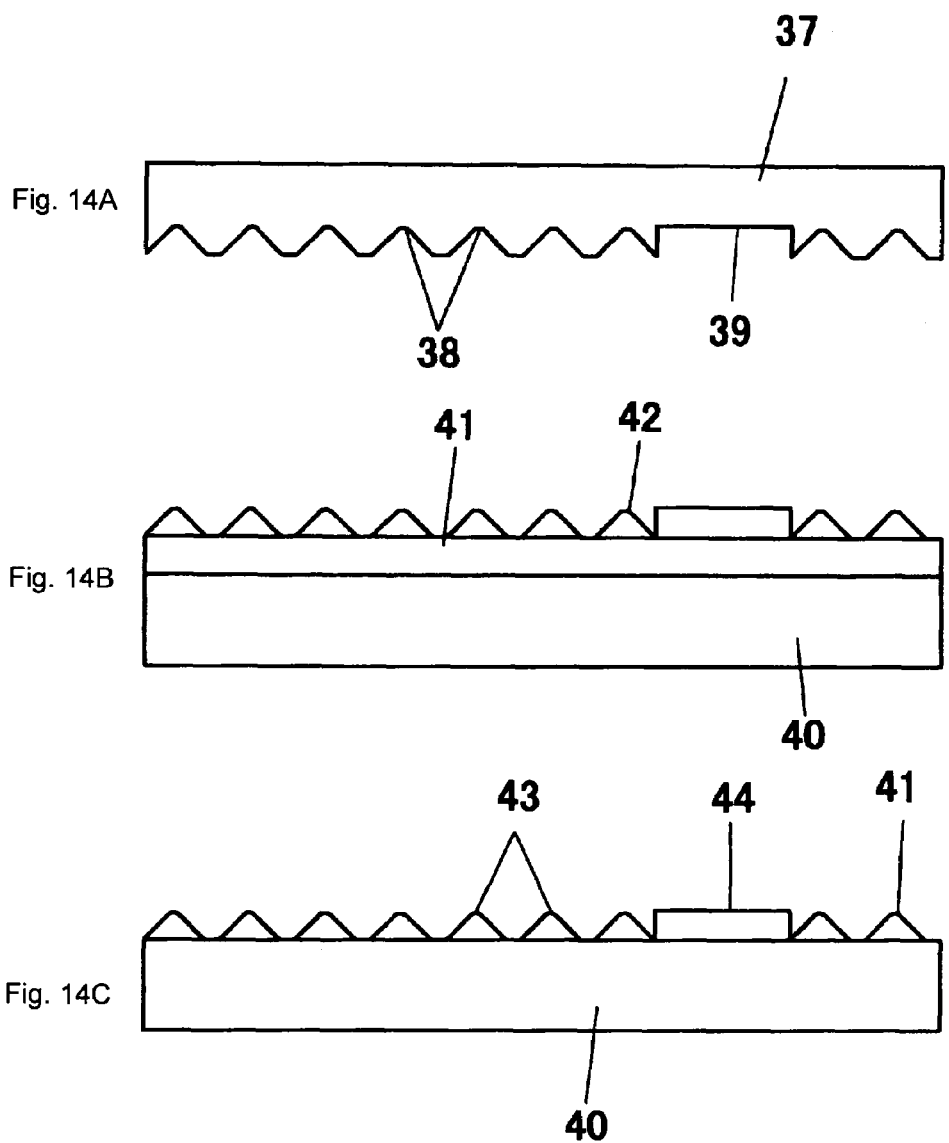
FIGS. 14A, 14B, and 14C show the schematic method of manufacturing quantum devices of the present invention.

FIGS. 14A, 14B, and 14C show the schematic manufacturing method of the quantum devices according to the present invention. A nano-stamper 37 shown in FIG. 14A has been manufactured in the same manner as that of the mother stamper 18 according to the first embodiment and on the bottom surface of the nano-stamper 37, nano-scale dents 36 (cavities 19) are formed using biomolecules as a template. In the case of a single electronic transistor, dents 39 are formed to obtain partially fine line structures by electron beam lithography or any other technique. As shown in FIG. 14B, a semiconductor layer 41 is formed on the top surface of a board 40, uncured resin 42 is applied to the semiconductor layer 41 and the resin-applied semiconductor 41 is pressed down by the nano-stamper 37 from the upper side to form the resin 42 using the dents 38 and 39. Then, by peeling the nano-stamper 37 after the resin 42 has been cured, the dot and fine line patterns are formed on the semiconductor 41 by the resin 42. After patterning has been applied to the semiconductor 41 by ion-etching using the patterns formed by the resin 42 as masks, by removing the resin 42, the quantum dots 43 and the fine lines 44 are obtained from the semiconductor 41.

According to the present invention, the manufactured quantum devices have nano-scale quantum dots and others are formed using the two-dimensional arrangement of biomolecules such as proteins and thereby, the uniformity in size among quantum dots and others is higher. In addition, using the self assembly feature of the proteins, the arrangement of biomolecules is facilitated. Furthermore, since the present invention uses the stampers (replicates), the nano-stamper 37 can be used to manufacture repeated quantum dots, enabling the mass-production of quantum devices.

If the quantum dots with a uniform size can be manufactured in this way, the quantum dot laser may be put in practical use earlier. In the case of a single electron transistor, by making the sizes of the quantum dots uniform, the voltage values such as the gate or bias voltages of the individual single electron transistors may be also made uniform.

Fourth Embodiment

Figure 15:
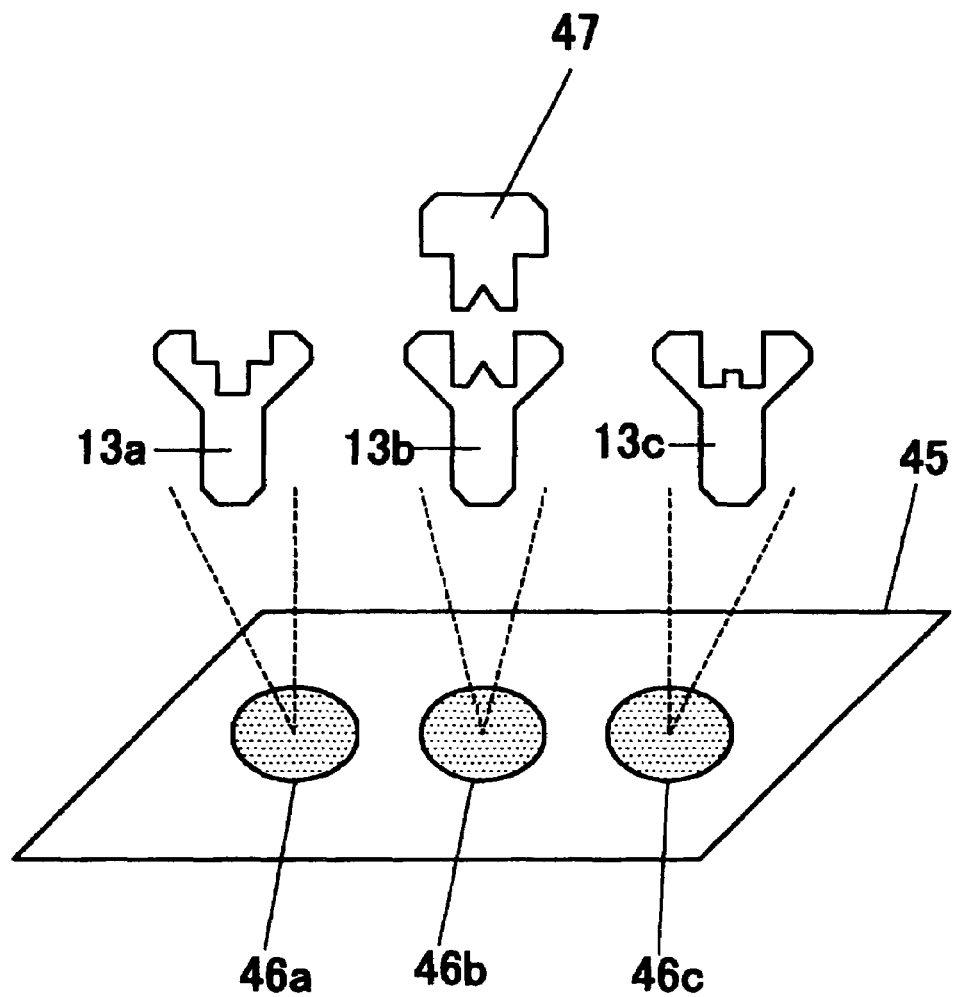
FIG. 15 shows the protein chip for disease diagnosis from the perspective point of view.

FIG. 15 shows the protein chip for disease diagnosis from the perspective point of view. A plurality of segments, 46a, 46b, and 46c, where different types of proves 13a, 13b, and 13c were immobilized, have been formed on the protein chip 15 as shown in the enlarged schematic drawing. For example, the segment 46a is the segment for detecting anthrax, where the probes 13a, proteins specifically binding to the targets such as proteins or antigens derived from anthrax, are immobilized. Similarly, the segment 46b is the segment for detecting smallpox, where the probes 13b, proteins specifically binding to the targets such as proteins or antigens derived from smallpox. The segment 46c is the segment for detecting influenza viruses, where the probes 13c, proteins specifically binding to the targets such as proteins or antigens derived from influenza viruses.

When blood, a possible test sample, is dropped o the protein chip 45, a target 47 (proteins in blood) contained in blood specifically binds to the binding sites of the probes binding specifically to the target 47. For example, in the case where the target 47 derived from a smallpox virus is contained in blood, the target 47 would bind to the probes 13b.

Figure 16:
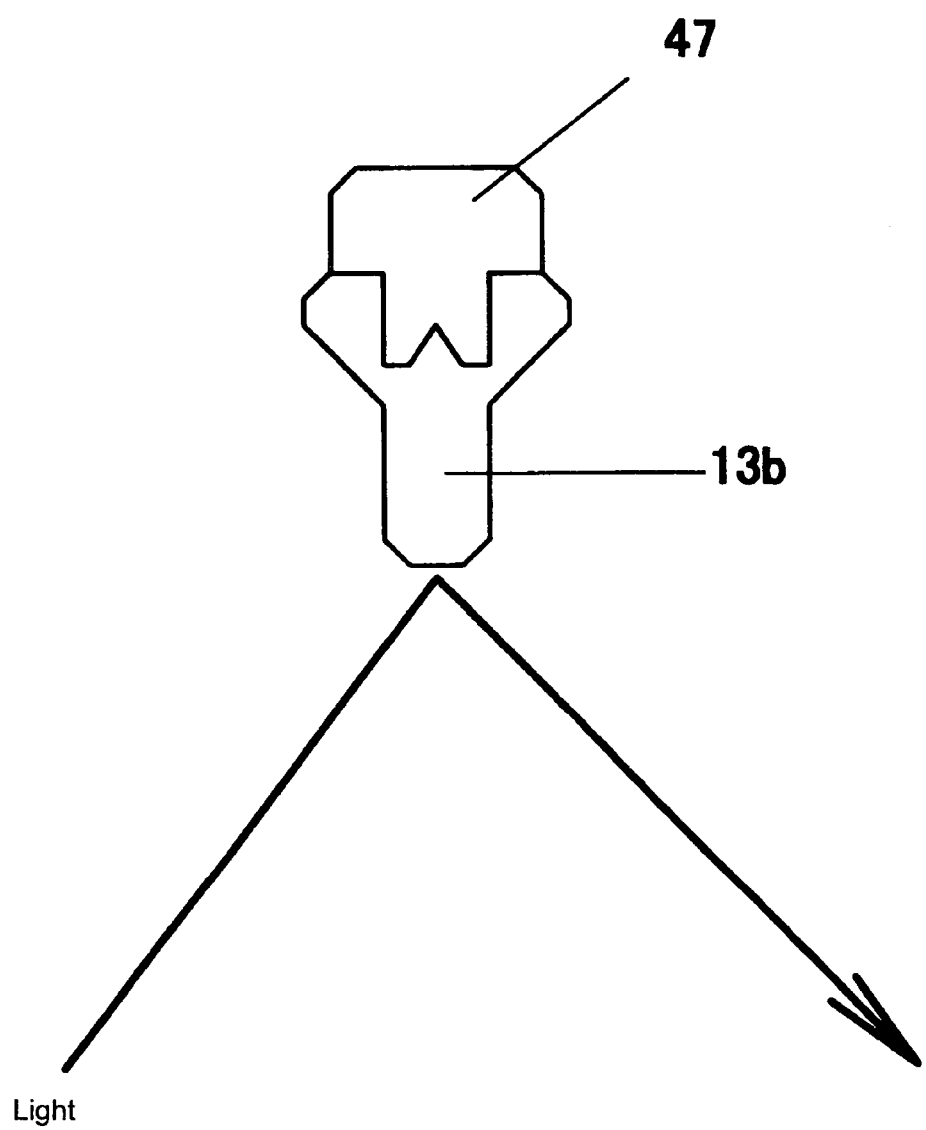
FIG. 16 shows the method of detecting any changes in probes immediately before and after the target is absorbed.

Since with respect to the individual probes 13a, 13b, and 13c, any changes appear in property immediately before and after the target is absorbed, after blood is dropped on the protein chip 45, a light beam is irradiated on the protein chip 45 as shown in FIG. 16 and the light reflected from the probes 13a, 13b, and 13c is received. By analyzing this light, it can be determined that an optical change may occur in which probes 13a, 13b or 13c and that if any, to how extent the light has changed. For example, assuming that a change has occurred in the probes 13b, it can be determined that the target derived from smallpox would be contained in blood and based on this result, the subject, from whom the blood sample was collected, would be diagnosed to be possibly infected with smallpox.

What is claimed is:

1. A method of transcribing biomolecular patterns comprising;
 a first step for two-dimensionally arranging biomolecules on a board, a second step for forming a thin film layer made of an inorganic substance on the biomolecules by sputtering or evaporating the inorganic substance under a condition of keeping a temperature of the board lower than 40° C., a third step for forming a supporting layer on the thin film layer that is directly formed on the biomolecules by electrotyping the same inorganic substance as the inorganic substance of the thin film layer, and a fourth step for peeling the thin film layer and the supporting layer off of the biomolecules together, thereby transcribing the biomolecular patterns wherein in the first step, the biomolecules are arranged such that the binding sites of the biomolecules are facing the surface of the board, and wherein the thin film is a means for fast replication of the pattern into a template, and wherein the supporting layer is a means for improving an overall strength of the template without adding to an overall processing time.

2. The method of transcribing biomolecular patterns of claim 1, wherein at least one of hydrophilic, hydrophobic, and electrifying treatments is applied to a segment on the board other than where the biomolecules are arranged before the biomolecules are arranged in the first step.

3. The method of transcribing biomolecular patterns of claim 1, wherein the biomolecules are arranged by two-dimensionally arranging antigens on the board followed by specific binding of the biomolecules to the antigens.

4. The method of transcribing biomolecular patterns of claim 1, wherein the top surface of the thin film layer is flatly formed in the second step.

5. The method of transcribing biomolecular patterns of claim 1, wherein almost a same level of pH value is used in the electrotyping as a level of pH value of the biomolecules in the third step.

6. The method of transcribing biomolecular patterns of claim 1, wherein the particle size of the inorganic substance composing the thin film layer is less than 50 nm.

7. The method of transcribing biomolecular patterns of claim 1, wherein the thickness of the thin film layer is less than 200 nm.

8. A method of manufacturing a chip board comprising;

a first step for two-dimensionally arranging biomolecules on a board, a second step for forming a thin film layer made of an inorganic substance on the biomolecules by sputtering or evaporating the inorganic substance under a condition of keeping a temperature of the board lower than 40° C., a third step for forming a supporting layer on the thin film layer that is directly formed on the biomolecules by electrotyping the same inorganic substance as the inorganic substance of the thin film layer, a fourth step for obtaining a first stamper having the concave parts of the reversed patterns of the biomolecules by peeling the thin film layer and the supporting layer off of the biomolecules together, a fifth step for manufacturing a second stamper having the patterns replicated from the biomolecular patterns, as templates, using the first stamper, and a sixth step for manufacturing the replicated patterns of the first stamper using the second stamper, thereby manufacturing the chip board wherein in the first step, the biomolecules are arranged such that the binding sites of the biomolecules are facing the surface of the board, and wherein the thin film is a means for fast replication of the pattern into a template, and wherein the supporting layer is a means for improving an overall strength of the template without adding to an overall processing time.

9. The method of manufacturing a chip board of claim 8, wherein the biomolecules are two-dimensionally arranged on the board using a self assembly feature of biomolecules in the first step.

10. A method of manufacturing a biochip comprising;

a first step for two-dimensionally arranging biomolecules on a board, a second step for forming a thin film layer made of an inorganic substance on the biomolecules by sputtering or evaporating the inorganic substance under a condition of keeping a temperature of the board lower than 40° C., a third step for forming a supporting layer on the thin film layer that is directly formed on the biomolecules by electrotyping the same inorganic substance as the inorganic substance of the thin film layer, and a fourth step for peeling the board off, thereby manufacturing the biochip wherein in the first step, the biomolecules are arranged such that the binding sites of the biomolecules are facing the surface of the board, and wherein the thin film is a means for fast replication of the pattern into a template, and wherein the supporting layer is a means for improving an overall strength of the template without adding to an overall processing time.

11. A method of manufacturing a biochip comprising;

a first step for two-dimensionally arranging biomolecules on a board, a second step for forming a thin film layer made of an inorganic substance on the biomolecules by sputtering or evaporating the inorganic substance under a condition of keeping a temperature of the board lower than 40° C., a third step for a forming a supporting layer on the thin film layer that is directly formed on the biomolecules by electrotyping the same inorganic substance as the inorganic substance of the thin film layer, and a fourth step for obtaining a first stamper having the concave parts of the reversed patterns of the biomolecules by peeling the thin film layer and the supporting layer off of the biomolecules together, a fifth step for manufacturing a second stamper having the patterns replicated from the biomolecular patterns, as templates, using the first stamper, a sixth step for manufacturing the replicated patterns of the first stamper using the second stamper, and a seventh step for immobilizing given biomolecules in concave parts disposed at the replicated patterns of the first stamper, thereby manufacturing the biochip wherein in the first step, the biomolecules are arranged such that the binding sites of the biomolecules are facing the surface of the board, and wherein the thin film is a means for fast replication of the pattern into a template, and wherein the supporting layer is a means for improving an overall strength of the template without adding to an overall processing time.

* * * * *